United States Patent [19]

Randklev

[11] 4,350,532

[45] Sep. 21, 1982

[54] GLASS COMPOSITION AND ARTICLES

[75] Inventor: Ronald M. Randklev, White Bear Lake, Minn.

[73] Assignee: Minnesota Mining and Manufacturing Company, St. Paul, Minn.

[21] Appl. No.: 288,290

[22] Filed: Jul. 30, 1981

Related U.S. Application Data

[63] Continuation-in-part of Ser. No. 184,917, Sep. 8, 1980, abandoned.

[51] Int. Cl.$^3$ .......................... A61K 6/04; C03C 1/04
[52] U.S. Cl. ...................................... 106/30; 106/26; 260/998.11; 501/102
[58] Field of Search ............................ 501/26, 30, 57; 260/998.11

[56] References Cited

U.S. PATENT DOCUMENTS

| | | | |
|---|---|---|---|
| 2,523,266 | 9/1950 | Armistead | 106/53 |
| 3,413,133 | 11/1968 | Stalego | 106/50 |
| 3,661,601 | 5/1972 | Dumbaugh et al. | 106/54 |
| 3,715,331 | 2/1973 | Melner | 260/41 B |
| 3,728,139 | 4/1973 | Carrier et al. | 106/54 |
| 3,801,344 | 4/1974 | Dietz | 106/300 |
| 3,808,170 | 4/1974 | Rogers | 260/42.53 |
| 3,826,778 | 7/1974 | Dietz | 260/42.47 |
| 3,873,327 | 3/1975 | Duff | 106/35 |
| 3,882,080 | 5/1975 | Schmitt et al. | 260/42.29 |
| 3,911,581 | 10/1975 | Dietz | 32/15 |
| 3,959,212 | 5/1976 | Rockett et al. | 260/42.53 |
| 3,971,754 | 7/1976 | Jurecic | 260/42.15 |
| 3,973,972 | 8/1976 | Muller | 106/39.7 |
| 3,975,203 | 8/1976 | Dietz | 106/299 |
| 4,017,454 | 4/1977 | Müller | 260/42.52 |
| 4,028,325 | 6/1977 | King et al. | 260/42.15 |
| 4,032,504 | 6/1977 | Lee, Jr. et al. | 260/42.18 |
| 4,050,947 | 9/1977 | Ahlgren et al. | 106/52 |
| 4,215,033 | 7/1980 | Bowen | 260/42.15 |
| 4,217,264 | 8/1980 | Mabie et al. | 260/42.15 |
| 4,250,277 | 2/1981 | Maries et al. | 525/337 |

OTHER PUBLICATIONS

R. L. Bowen and L. E. Reed, "Semiporous Reinforcing Fillers for Composite Resins: I. Preparation of Provisional Glass Formulations", *J. Dent. Res.*, 55, 5, pp. 738-747, (1976).

R. L. Bowen and L. E. Reed, "Semiporous Reinforcing Fillers for Composite Resins: II. Heat Treatments and Etching Characteristics", *J. Dent. Res.*, 55, 5, pp. 748-756, (1976).

Ingerson et al., Am. Journal of Science, 246:31-4 (1948).

Ushakov et al., "Influence of Replacement of Silica by Various Glass-Forming Oxides on the Tendency to Phase Separation in the System $R_2O—B_2O_3—SiO_2$", pp. 103-106, *The Structure of Glass*, vol. 8, (Ed. by Porai-Koshits), pub. by Consultants Bureau, New York 1973.

Bal'skaya, L. A. et al., "Phase Separation in Low-Alkali Borosilicate Glasses Containing RO and $Al_2O_3$", pp. 107-113, *The Structure of Glass*.

Grenchanik, L. A. et al., "Properties of Glasses Exhibiting Phase Separation in the System, $SiO_2—B_2O_3—Al_2O_3—ZnO—Na_2O$", pp. 114-117, *The Structure of Glass*.

Milyukov, E. M. et al., "Phase-Separation Phenomena in Glasses of Aluminosilicate Systems Containing Various Modifier Cations", pp. 158-161, *The Structure of Glass*.

*Primary Examiner*—G. O. Peters
*Attorney, Agent, or Firm*—Cruzan Alexander; Donald M. Sell; David R. Cleveland

[57] ABSTRACT

This invention provides a novel glass composition having numerous uses. More particularly, the invention provides a single phase, radiopaque glass composition.

4 Claims, No Drawings

GLASS COMPOSITION AND ARTICLES

CROSS-REFERENCE TO RELATED APPLICATION

This application is a continuation-in-part of my copending application Ser. No. 184,917, filed Sept. 8, 1980, now abandoned.

BACKGROUND ART

Glass compositions have been used in various medical and dental prostheses, hard tissue cements, and dental filling compositions. It is highly desirable for a medical or dental prosthesis, hard tissue cement, or dental filling composition to be radiopaque so that it is detectable by X-rays. For example, from radiographs a dentist determines the condition of a dental filling, e.g. whether it has cracked, or whether decay is occurring at the interface between the tooth and the filling. Fillings and restorations which are made of metal are readily observable in X-rays. Fillings of the porcelain/plastic art are not observable by X-rays unless they have radiopaque materials therein.

Currently, dental filling materials are rendered radiopaque by incorporating barium into the inorganic powder moiety of the filling material. The most effective radiopaque agents are elements of high atomic number (i.e. the "heavy elements" of the periodic table); it is unfortunate, however, that most of these elements are either radioactive or toxic, such as thorium or lead. Barium is toxic also, but in certain medical uses it is present in a form so highly insoluble that the body is unable to metabolize enough of it to become intoxicated. In dental applications barium glasses have been used as components of dental restorations, on the hypothesis that barium ions within the structure of a glassy matrix will not be available to oral fluids (saliva, beverages, etc.) and will not, therefore, pose a problem of toxicity. Examples of the use of barium glass in dental restorations can be found in U.S. Pat. Nos. 3,801,344; 3,808,170; 3,826,778; 3,911,581; 3,959,212; 3,975,203 and 4,032,504. Unfortunately, in practice, the barium glasses are not as stable as had originally been hoped, and they have not, therefore, found favor in the art on account of the risk they pose of poisoning the patient (see, e.g. U.S. Pat. No. 3,971,754). A further problem encountered with the barium glasses is that of matching refractive indices to that of the other components of the restoration. For example, it would be desirable to use components with refractive indices in the range of about 1.5 to 1.6 (so as to closely match the refractive index of commonly used organic binders) but most barium glasses with refractive indices in this range are unsuitable for dental use according to U.S. Pat. No. 4,032,504. It is difficult, therefore, to prepare restorations containing barium glass which present an unobtrusive appearance when used for anterior surface repair. An additional problem of the barium glasses is their alkalinity. Typically, barium glasses show alkalinity values of pH 9 or greater, whereas a pH of 7 is preferred. Highly alkaline fillers appear to degrade the siloxane coating resulting from etching of the prepared tooth cavity and also cause rapid decomposition of any peroxide catalyst present in the dental restorative composition during storage.

Recent efforts in the field of dental restoration materials have resulted in the use of fillers other than barium-containing compounds as an X-ray detectable component. For example, U.S. Pat. No. 3,971,754 describes the use of certain oxides or carbonates, particularly those of lanthanum, strontium, tantalum and, less usefully, hafnium. These salts are mixed with glass-making components at the time the glass is made, yielding a lanthanum, strontium, tantalum or hafnium glass which possesses a measure of radiopacity. U.S. Pat. Nos. 3,973,972 and 4,017,454 describe glass ceramics which possess both a low coefficient of thermal expansion (an advantage in dental fillings) and a useful degree of radiopacity, by virtue of a high content of rare earth elements, particularly lanthanum. The rare earth elements absorb X-rays in the wavelength range of 0.2-0.3A, a range commonly available from dental X-ray machines. However, the cost and problems with availability of these rare earth fillers make them generally unsuitable for commercial use.

In another approach to preparing radiopaque composites for dental use, organic halide (e.g. an alkyl iodide) has been incorporated into plastic materials (e.g. acrylate polymers), from which molded articles are made (e.g. U.S. Pat. No. 3,715,331). However, the articles molded from such compositions lack the strength of restorations made from glass or ceramic materials.

U.S. Pat. No. 4,250,277 describes a glass composition used for crosslinking polycarboxylic acid cement, wherein the glass contains zinc oxide and a large amount of boric oxide, in addition to other ingredients. This glass, however, is too water soluble to be useful in dental restorative compositions and prosthetic devices.

U.S. Pat. No. 4,215,033 describes a composite dental material containing a glass which in one embodiment is described as single phase. However, the patent does not appear to recognize that a single phase glass containing zinc oxide can be made radiopaque. Also, the single phase glass composition described in this patent is very difficult to make. Furthermore, such glass does not contain any aluminum fluoride.

DISCLOSURE OF INVENTION

In accordance with the present invention there is provided a single phase glass composition consisting essentially of, in percent by weight:

| | |
|---|---|
| Zinc oxide | 20 to 35% |
| Silica | 45 to 65% |
| Boric oxide | 3 to 15% |
| Aluminum oxide | 0 to 10% |
| Aluminum fluoride | At least 2% |
| Alkali metal oxide or alkaline earth metal oxide | 0 to 5% | wherein the combined weight of aluminum oxide and aluminum fluoride is at least about 5%, and wherein said composition exhibits an X-ray absorption characteristic of at least 1/16 inch. The presence of the aluminum fluoride is extremely important because it contributes to the melt fluidity of the glass and enables it to be poured in the form of thin filaments for rapid cooling thereof.

The glass compositions of this invention are particularly useful for use in hard tissue cements (i.e. bone cements and tooth cements), medical and dental prostheses (e.g. catheters, valves, dental bridges, etc.), pit and fissure sealants, dental restorative compositions, and the like. The novel glass compositions are particularly desirable because they are nontoxic, have desirable radiopacity, and have a neutral pH. Dental restorative compositions containing the novel glass compositions are described in my copending application Ser. No. 288,289, filed of even date, incorporated herein by reference, which is a continuation-in-part of my earlier application Ser. No. 184,916, filed Sept. 8, 1980.

DETAILED DESCRIPTION

It has been discovered that glasses containing high levels of zinc can be prepared which possess physical characteristics (e.g. refractive index, pH, coefficient of expansion) making them especially suitable for use in dental prostheses, dental restorative compositions, hard tissue cements, medical prostheses, and other articles. Moreover, these glasses have been found to be radiopaque and to be capable of being made into dental composites and other articles which have greater radiopacity than those made with barium, the best known radiopacifying agent used heretofore. This is quite surprising, considering barium has an atomic number of 56, iodine an atomic number of 53, the lanthanides having atomic numbers of 57 to 71, and zinc having an atomic number of only 30. Moreover, it has been found possible to make the new zinc glasses with refractive indices in the desired range for dental restorative compositions. In addition, the new glasses can be prepared at a pH close to 7. This is a highly desirable feature in regard to the preparation of high quality dental composites. In particular, when the glass is near neutral in pH (i.e. 6.5 to 8), the stability of the dental composite is significantly enhanced. Improved stability is exhibited as longer shelf life, improved color stability, and reliable setting characteristics after the activated composite is emplaced in the tooth being repaired. The new glasses are significantly better than the barium glasses of the prior art in this regard.

It is believed that the problems encountered with the barium glasses are contributed to by the relative alkalinity of such materials. Barium is an alkaline earth element in the periodic system, and, therefore, more electropositive than zinc, which is a transition element. The higher pHs characteristic of the barium glasses cause decomposition of the peroxide catalysts normally used in these formulations and thus greatly reduce storage stability. A significant advantage of the new glasses, which is an improvement over any known heretofore, is that they contain an element, namely, zinc, that has been in regular dental use for many years. Zinc oxide-containing ointments have long been used in medicine as safe and mild antibacterial agents and zinc oxide has long been used as a component in dental cements or adhesives. These latter agents are used for cementing prostheses, onlays, bridges, crowns, and the like, to the teeth. In this use they have proved safe and effective over many years. In other words, zinc compounds have a long history of being safe to use in the oral cavity, and are thus vastly preferable to use compared with those of unknown safety or known toxicity, such as compounds of barium.

The new glasses of this invention have the following composition in percent by weight:

| Zinc oxide | (ZnO) | 20 to 35% |
|---|---|---|
| Silica | ($SiO_2$) | 45 to 65% |
| Boric oxide | ($B_2O_3$) | 3 to 15% |
| Aluminum oxide | ($Al_2O_3$) | 0 to 10% |
| Aluminum fluoride | ($AlF_3$) | At least 2% |
| Alkali metal oxide | | 0 to 5% |
| or alkaline earth metal oxide | | | wherein the combined weight of aluminum oxide and aluminum fluoride is in the range of at least about 5%, and wherein said composition exhibits an X-ray absorption characteristic of at least 1/16 inch. The alkali metal oxide or alkaline earth metal oxide may be, for example, sodium oxide, potassium oxide, lithium oxide, calcium oxide, magnesium oxide, or the like, or combinations thereof. Preferably the combined weight of such oxides does not exceed about 3% of the glass, thus maintaining the pH of the glass in the desired range of about 6.5 to 8, when the glass is intended for dental applications. When the glass is intended for other applications, or where storage stability is less important, the pH of the glass is not as critical. Of course, as will be recognized by those skilled in the art, various other ingredients may also be present in minor amounts so long as the resulting glass exhibits the desired X-ray opacity and the desired pH. However, it is highly preferred to avoid the inclusion of toxic metals such as lead, cadmium, mercury, arsenic, etc.

A preferred embodiment of the new glass for use in dental restoratives has the following compositions:

| Zinc oxide | 25 to 28% |
|---|---|
| Silica | 46 to 48% |
| Boric oxide | 6 to 9% |
| Aluminum oxide | 1 to 3% |
| Aluminum fluoride | 17 to 19% | wherein the combined weight of aluminum oxide and aluminum fluoride is not greater than about 20%, and wherein said composition exhibits an X-ray absorption characteristic of at least 3/32 inch.

The compositions given above are written in terms of the salts (e.g. oxides and fluorides) which are used in preparing the melt from which the glass is obtained upon cooling. This is a common practice in the glass-making art. There is, of course, no oxide, fluoride, or other simple salt in the resultant glass. Glasses used in this invention all possess a useful degree of radiopacity.

The refractive index of the glass may be varied, depending upon the particular amount of each ingredient present. It is preferred that the refractive index of the glass filler be substantially the same as that of the binder resin when the glass is used in a dental filling composition, i.e. within about 0.05, when the composition is used in anterior applications. When the binder resin comprises the well-known BIS-GMA, the refractive index for the glass filler is preferably 1.556+0.05. Matching of the refractive indices of the glass filler and the binder resin is less important when the composition is intended for posterior dental applications.

When BIS-GMA resin is diluted with another acrylic resin (e.g. triethyleneglycol dimethacrylate) to facilitate higher filler loadings to make a composition having particular use for posterior filling applications, the resultant resin mixture may have a refractive index of 1.545, for example. Consequently, for such an application it may be preferred to use a glass composition of the invention having a refractive index of 1.545 if close matching of the resin and filler is desired. When it is desired to prepare a dental filling composition which is light curable it is important to obtain a close match of the refractive indices of the polymerizable resin and the glass filler so that complete and rapid cure of the resin will be achieved when it is exposed to the activating light. Of course, when the composition is intended for use elsewhere in the body (i.e. where esthetics are not a factor) and where the composition is not light curable, there is no need to attempt matching the refractive index of the glass to the refractive index of the binder resin.

Radiopacity, which reflects the material's ability to attenuate X-rays, is conveniently measured by comparing the X-ray film image density values of a disc of the cured composite of a standard thickness, e.g. 0.040 inches, with corresponding values of a known standard. Film image density measurements are made with a suitable densitometer, such as a Macbeth Transmission Densitometer, Model TD 504, with visible light filter (manufactured by Macbeth Div. of Kollmorgan Corp., Newburgh, N.Y.). A convenient standard for determining the radiopacity of glass of this invention is a stepped aluminum wedge, for example, a ten step wedge having a thickness of 1/32 inches at the thinnest step increasing to 5/16 inches at the thickest step. One empirically determines the X-ray film image density values corresponding to steps on the wedge, which indicate degrees of X-ray beam attenuation which provide, in actual practice, proper differentiation, for example, between a composite restoration and the surrounding tooth structure. A proper level of radiopacity will permit one skilled in the art to differentiate between the restoration and primary and recurrent caries in the tooth structure, and will also visualize defects in the restoration itself. By way of illustration, using a wedge, the glasses of this invention when tested in this manner give values of 1/16 inch at 26% ZnO; 3/32-⅛ inch at 26.5–28% ZnO. Typical barium glasses of the prior art, tested under identical conditions give values of 1/16–3/32 inch. The typical "plastic" or "porcelain" filling materials (containing quartz or borosilicate filler) common in contemporary dental practice give values of zero. A silver amalgam gives a value of >5/16 inch. It will be understood, of course, that these values are completely empirical. Using different wedges and experimental apparatus, the actual numbers one gets may be different. For the purposes of this invention the glass must exhibit an "X-ray absorption characteristic" of at least 1/16 inch.

Insofar as the preparation of the zinc glass is concerned, standard techniques well-known in the glass-making art are used. See, for example, The Handbook of Glass Manufacture, Fay and Tooley, Volume I (1974). After the melt has cooled, the glass is comminuted to a size that passes through a 325-mesh standard sieve (44 microns) For grinding the glass into smaller sizes a ball mill is used, and grinding aids such as ammonium carbonate or alcohols may be present in an amount of approximately 0.5% based on the weight of the glass.

When making dental composite restorative, the glass powder is then prepared for incorporating into an organic binder matrix by treating the surface with a silane compound. This is a well-known technique for rendering relatively polar materials, such as siliceous powders, more compatible with relatively non-polar materials, such as organic polymers.

The zinc glass is then mixed into a dental paste. The paste may be formed of any of the polymerizable resin systems useful in dentistry. Especially useful resin systems comprise free-radically polymerizable materials such as the polyfunctional acrylate systems. Particularly useful in the system is BIS-GMA, a well-known material which is the reaction product of bisphenol-A and glycidyl methacrylate, widely used in dentistry. Other commonly used resin binders include polyurethanes, methyl methacrylate, and isobutyl methacrylate.

The zinc glass may be used alone or it may be blended with other suitable materials, such as inert glass powders, when mixed into the binder-depending, for example, on the degree of radiopacity desired in the final composite. Along with the glass, other materials may also be mixed into the paste, such as pigments for making the restoration match the patient's natural tooth color, and reagents like hydroquinone monomethyl ether, as an inhibitor of premature polymerization of the binder. Immediately before use, and after the dentist has prepared the tooth for receiving the restoration, the paste is activated by mixing into it the appropriate amount of catalyst, such as benzoyl peroxide. For example, the dental restorative composition may be in the form of two pastes (one paste containing filler, resin binder and catalyst while the other contains filler, resin binder and accelerator), or a liquid resin and powdered filler system, or a paste-liquid system, or any other desired form. The mixed composition is promptly emplaced in the tooth, hardening in the manner characteristic of the resin binder and catalyst system being used. For example, using the well-known BIS-GMA/benzoyl peroxide system, the composite becomes grossly rigid in about 5 minutes and may be finely ground and polished, to give the finished restoration, in about 10 minutes. At any time after emplacement, but more particularly after significant time has elapsed, such as many months or years afterwards, the condition of the restoration and the adjacent tooth structures can be determined by diagnostic dental X-rays.

Curable compositions which contain the novel glass and which are useful in other applications (e.g. medical and dental prostheses, pit and fissure sealants, hard tissue cements) may be prepared in similar fashion using polymerizable resin binders.

The invention is further illustrated by means of the following representative examples wherein the term "parts" refers to parts by weight unless otherwise indicated.

EXAMPLE 1

Silica (47 gms), zinc oxide (26 gms), boric oxide (8 gms), aluminum oxide (1 gm) and aluminum fluoride fluoride (18 gms) are thoroughly mixed, as fine powders, in a silica-lined crucible. The mixture is heated in a muffle furnace at 1450° until the powder has become a transparent melt.

The molten glass is then removed from the crucible through a small hole in the crucible wall, by tilting the crucible and allowing a thin stream of glass to flow through, giving a filament of glass of about 1/32 inch diameter. This filament is quenched rapidly in cold water, to give a completely clear glass (as opposed to being opalescent). Mere air cooling of the glass is not sufficiently rapid to prevent phase separation.

The clear glass is then ground, i.e. in a ball mill, to a mean particle size range of 0.5–15 μm.

EXAMPLE 2

Gamma-methacryloxy-propyltrimethoxy silane (2 gms) is mixed with glacial acetic acid (0.033 gms) and water (44.4 gms) in a plastic beaker. Glass powder (100 gms for example, from Example 1) is added to the mixture, and the system is stirred for 1.5 hours at room temperature. The glass slurry is dried by warming it at 140° F. (60 C.) for 24 hours, followed by heating it in an oven for 2.5 hours at 240° F. (115° C.).

EXAMPLE 3

Two pastes, A and B, are prepared, having the following compositions:

| Ingredient | Paste A | Paste B |
|---|---|---|
| BIS—GMA resin | 14.48 gm | 14.67 gm |
| Triethylene glycol dimethacrylate | 4.67 | 4.63 |
| Silane-treated filler (from Example 2) | 80.0 | 80.0 |
| Benzoyl peroxide | — | .21 |
| Dihydroxyethyl p-toluidine | .46 | — |
| "Tinuvin P", a UV absorber | .16 | — |
| Phenylsalicylate glycidyl methacrylate adduct, a UV absorber | .14 | .16 |
| Butylated hydroxytoluene | — | .16 |
| Bisphenol A | — | .14 |
| Pigments-titanium dioxide and iron oxides - (yellow raw sienna, burnt umber), ottalume | .17 | .17 |
| TOTAL | 100.00 gm | 100.00 gm |

The pastes are prepared as follows:

For each paste, A and B, two preliminary mixes are made. The glass (from Example 2) and the pigments are mixed thoroughly to give an evenly colored powder. This mix is the same for each paste. The resins, accelerator, UV absorbers and inhibitor are mixed to give the mix for paste A. The resins, catalyst, UV absorber, and inhibitor are mixed to give the mix for past B. After the two mixes, glass and resin based respectively, have been prepared, the procedure for preparing each paste, A and B, is the same.

Each resin mix is added to a vessel and then the respective glass mix is added. The two mixes are first roughly blended together, such as by shaking, and are then thoroughly mixed preferably by prolonged mechanical mixing.

The resultant homogeneous pastes, A and B, are the precursors to the dental restorations made from the materials of this invention. Pastes A and B are kept separate until immediately before the appropriate repair is made in a tooth which has been prepared to receive it. They are then mixed together thoroughly and promptly emplaced in the manner well-known in dental art.

EXAMPLE 4

A glass composition is prepared in accordance with the procedure of Example 1 using the following ingredients in the amounts stated:

| Silica | 50 grams |
|---|---|
| Zinc oxide | 33 grams |
| Boric oxide | 5 grams |
| Aluminum oxide | 8 grams |
| Sodium oxide | 4 grams |

The index of refraction of the resulting single phase glass is 1.566, and the visual opacity is 0.25. The pH of the glass is determined to be 8.5.

EXAMPLE 5

A glass composition is prepared in accordance with the procedure of Example 1 using the following ingredients in the amounts stated:

| Silica | 47.5 grams |
|---|---|
| Zinc oxide | 28.0 grams |
| Boric oxide | 5.0 grams |
| Aluminum oxide | 1.0 gram |
| Aluminum fluoride | 18.0 grams |
| Potassium oxide | 0.5 gram |

The index of refraction of the resulting single phase glass is 1.565, and the visual opacity is 0.23–0.24. The pH of the glass is determined to be 7.5.

EXAMPLE 6

A glass composition is prepared in accordance with the procedure of Example 1 using the following ingredients in the amounts stated:

| Silica | 47.5 grams |
|---|---|
| Zinc oxide | 26.5 grams |
| Boric oxide | 6.0 grams |
| Aluminum oxide | 1.0 gram |
| Aluminum fluoride | 17.0 grams |

The index of refraction of the resulting single phase glass is 1.560, and the visual opacity is 0.22. The pH is determined to be 7.3.

EXAMPLE 7

A glass composition is prepared in accordance with the procedure of Example 1 using the following ingredients in the amounts stated:

| Silica | 48.5 grams |
|---|---|
| Zinc oxide | 27.0 grams |
| Boric oxide | 5.0 grams |
| Aluminum fluoride | 18.0 grams |
| Potassium oxide | 0.5 gram |

The index of refraction of the resulting single phase glass is 1.561, and the visual opacity is 0.22. The pH of the glass is determined to be 7.5.

Other variants are permissible without departing from the scope of the present invention.

EXAMPLE 8

A glass composition is prepared in accordance with the procedure of Example 1 using the following ingredients in the amounts listed:

| Silica | 47.0 grams |
|---|---|
| Zinc oxide | 26.0 grams |
| Boric oxide | 8.0 grams |
| Aluminum oxide | 1.0 gram |
| Aluminum fluoride | 18.0 grams |

The index of refraction of the resulting single phase glass is 1.556 and the visual opacity is 0.13–0.15. The pH is determined to be 7.0–7.1.

EXAMPLE 9

A glass composition is prepared in accordance with the procedure of Example 1 using the following ingredients in the amounts listed:

| | |
|---|---|
| Silica | 48.0 grams |
| Zinc oxide | 25.0 grams |
| Boric oxide | 8.0 grams |
| Aluminum oxide | 1.0 gram |
| Aluminum fluoride | 18.0 grams |

The index of refraction of the resulting single phase glass is 1.545 and the visual opacity is 0.13. The pH is determined to be 7.0–7.1.

When the molten glass composition of this example is cooled by conventional methods the glass forms two phases spontaneously, with the crystallized phase having a different refractive index than the matrix glass. The resulting birefringent glass has high visual opacity which can preclude light curing of a dental composite containing such glass.

I claim:

1. A single phase glass composition consisting essentially of, in percent by weight:

| | |
|---|---|
| Zinc oxide | 20 to 35% |
| Silica | 45 to 65% |
| Boric oxide | 3 to 15% |
| Aluminum oxide | 0 to 10% |
| Aluminum fluoride | At least 2% |
| Alkali metal oxide or alkaline earth metal oxide | 0 to 5% | wherein the combined weight of aluminum oxide and aluminum fluoride is in the range of at least about 5%, and wherein said composition exhibits an X-ray absorption characteristic of at least 1/16 inch.

2. A composition in accordance with claim 1, wherein said glass consists essentially of, in percent by weight:

| | |
|---|---|
| Zinc oxide | 25 to 28% |
| Silica | 46 to 48% |
| Boric oxide | 6 to 9% |
| Aluminum oxide | 1 to 3% |
| Aluminum fluoride | 17 to 19% | wherein the combined weight of aluminum oxide and aluminum fluoride is not greater than about 20%.

3. A composition in accordance with claim 1, wherein said composition exhibits an X-ray absorption characteristic of at least 3/32 inch.

4. A prosthesis comprising a glass composition of claim 1.